US012220268B2

(12) United States Patent
Gou et al.

(10) Patent No.: US 12,220,268 B2
(45) Date of Patent: Feb. 11, 2025

(54) METHOD FOR IMAGE GUIDANCE, MEDICAL DEVICE AND COMPUTER-READABLE STORAGE MEDIUM

(71) Applicant: OUR UNITED CORPORATION, Shaanxi (CN)

(72) Inventors: Tianchang Gou, Shaanxi (CN); Hao Yan, Shaanxi (CN)

(73) Assignee: Our United Corporation, Shaanxi (CN)

( * ) Notice: Subject to any disclaimer, the term of this patent is extended or adjusted under 35 U.S.C. 154(b) by 576 days.

(21) Appl. No.: 17/615,063

(22) PCT Filed: May 29, 2019

(86) PCT No.: PCT/CN2019/089073
§ 371 (c)(1),
(2) Date: Nov. 29, 2021

(87) PCT Pub. No.: WO2020/237537
PCT Pub. Date: Dec. 3, 2020

(65) Prior Publication Data
US 2022/0218298 A1 Jul. 14, 2022

(51) Int. Cl.
*A61B 6/04* (2006.01)
*A61B 5/055* (2006.01)
(Continued)

(52) U.S. Cl.
CPC .............. *A61B 6/04* (2013.01); *A61B 5/055* (2013.01); *A61B 6/02* (2013.01); *A61B 6/032* (2013.01);
(Continued)

(58) Field of Classification Search
CPC ..... A61B 6/02; A61B 6/022–027; A61B 6/03; A61B 6/032–037
See application file for complete search history.

(56) References Cited

U.S. PATENT DOCUMENTS

2015/0243025 A1 8/2015 Berlinger et al.
2018/0056090 A1 3/2018 Jordan et al.

FOREIGN PATENT DOCUMENTS

CN 102232835 A 11/2011
CN 103068443 A 4/2013
(Continued)

OTHER PUBLICATIONS

China National Intellectual Property Administration, First office action of Chinese application No. 201980096948.2 issued on May 31, 2023.
(Continued)

*Primary Examiner* — Colin T. Sakamoto
(74) *Attorney, Agent, or Firm* — Knobbe, Martens, Olson & Bear, LLP

(57) ABSTRACT

The present disclosure provides a method and apparatus for image guidance, a medical device and a computer-readable storage medium. The method for image guidance includes: controlling an imaging mechanism to rotate around a patient positioning mechanism; acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; performing, after a second image corresponding to the first image is acquired, image guidance using a combination of the first image and the second image as an indicator of a current position state of the patient.

20 Claims, 4 Drawing Sheets

(51) Int. Cl.
*A61B 6/00* (2024.01)
*A61B 6/02* (2006.01)
*A61B 6/03* (2006.01)
*G06T 7/30* (2017.01)
*A61N 5/10* (2006.01)
*G06T 7/246* (2017.01)
*G06T 7/73* (2017.01)

(52) U.S. Cl.
CPC .......... *A61B 6/5235* (2013.01); *A61B 6/5247* (2013.01); *G06T 7/30* (2017.01); *A61B 6/5223* (2013.01); *A61N 2005/1055* (2013.01); *A61N 2005/1061* (2013.01); *A61N 2005/1062* (2013.01); *A61N 2005/1063* (2013.01)

(56) References Cited

FOREIGN PATENT DOCUMENTS

| CN | 104888356 A | 9/2015 |
|---|---|---|
| CN | 106408509 A | 2/2017 |
| WO | 2018044718 A1 | 3/2018 |

OTHER PUBLICATIONS

International search report of PCT application No. PCT/CN2019/089073 issued on Feb. 28, 2020.

METHOD FOR IMAGE GUIDANCE, MEDICAL DEVICE AND COMPUTER-READABLE STORAGE MEDIUM

CROSS REFERENCE TO RELATED APPLICATION

This application is a 371 of PCT Patent Application Serial No. PCT/CN2019/089073, filed on May 29, 2019, the entire contents of which are herein incorporated by reference.

TECHNICAL FIELD

The present disclosure relates to the field of medical imaging, and in particular to a method and apparatus for image guidance, a medical device and a computer-readable storage medium.

BACKGROUND

During radiotherapy, a motion of a target region in the same treatment subsection may result in deviation of the focus of a treatment beam from the treatment target region. To solve this problem, the deviation between the focus of the treatment beam and the target region position may be determined by using an image guidance technology based on images acquired in real time, and then corrected.

During image guidance, a current position state of the target region may be tracked by using an imaging apparatus of an X-ray transmitted image. The imaging apparatus may include an X-ray tube and a detector that are disposed oppositely, and an X-ray emitted by the X-ray tube passes through a target region of a patient and is then received by the detector to form the required X-ray transmitted image.

SUMMARY

The present disclosure provides a method and apparatus for image guidance, a medical device and a computer-readable storage medium.

According to a first aspect of the present disclosure, a method for image guidance is provided. The method is applied to a medical device which includes a patient positioning mechanism and an imaging mechanism. The imaging mechanism is configured to be capable of capturing medical images of a patient on the patient positioning mechanism at a plurality of capturing angles by rotating around the patient positioning mechanism. The method for image guidance includes:

controlling the imaging mechanism to rotate around the patient positioning mechanism;

acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and performing, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

In some possible embodiments, the capturing angles are a plurality of continuous capturing angles with the same angle interval, and controlling the imaging mechanism to rotate around the patient positioning mechanism includes:

controlling the imaging mechanism to rotate around the patient positioning mechanism at a constant speed, so that the imaging mechanism is continuously rotated to pass the capturing angles with the same time interval.

In some possible embodiments, the method further includes:

acquiring a two-dimensional projected image of a three-dimensional reconstructed image of the patient at each of the capturing angles, the three-dimensional reconstructed image being based on computed tomography;

correspondingly, performing image guidance using the combination of the first image and the second image as the indicator of the current position state of the patient includes:

acquiring a first registration result by performing 2D-2D registration between the first image and the two-dimensional projected image at the first capturing angle;

acquiring a second registration result by performing 2D-2D registration between the second image and the two-dimensional projected image at the second capturing angle; and correcting a relative position deviation between the current position state of the patient and an initial position state of the patient based on the first registration result and the second registration result.

In some possible embodiments, the method further includes:

acquiring a three-dimensional magnetic resonance image of the patient, wherein a region range of at least one object of interest is marked in the three-dimensional magnetic resonance image;

acquiring a three-dimensional reference image of the patient, wherein the three-dimensional reference image is a three-dimensional reconstructed image based on computed tomography; and marking a region range of each object of interest in the three-dimensional reference image by performing 3D-3D registration between the three-dimensional magnetic resonance image and the three-dimensional reference image;

correspondingly, performing image guidance using the combination of the first image and the second image as the indicator of the current position state of the patient includes:

performing image guidance using the three-dimensional reference image as an indicator of an initial position state of the patient and using the combination of the first image and the second image as the indicator of the current position state of the patient.

In some possible embodiments, performing image guidance using the three-dimensional reference image as an indicator of an initial position state of the patient and using the combination of the first image and the second image as the indicator of the current position state of the patient includes:

acquiring a third registration result by performing 2D-3D registration between the three-dimensional reference image and the combination of the first image and the second image; and correcting the relative position deviation between the current position state of the patient and the initial position state of the patient based on the third registration result.

In some possible embodiments, the method further includes:

performing error correction on the current position state of the patient indicated by the combination of the first image and the second image by using at least one dual two-dimensional image combination after at least one third image corresponding to the first image is required;

the dual two-dimensional image combination is a combination between the first image and one of the third images, the third image is a medical image of the patient captured by the imaging mechanism at a third capturing angle, and the third capturing angle is a capturing angle among the capturing angles which is at an angle smaller than a second preset angle with the second capturing angle.

In some possible embodiments, performing error correction on the current position state of the patient indicated by the combination of the first image and the second image by using at least one dual two-dimensional image combination includes:

calculating a state parameter indicating the current position state of the patient based on each dual two-dimensional image combination, respectively; and performing error correction on a state parameter calculated based on the combination of the first image and the second image by using the state parameter respectively corresponding to each dual two-dimensional image combination.

According to a second aspect of the present disclosure, an apparatus for image guidance is provided. The apparatus is applied to a medical device which includes a patient positioning mechanism and an imaging mechanism. The imaging mechanism is configured to be capable of capturing medical images of a patient on the patient positioning mechanism at a plurality of capturing angles by rotating around the patient positioning mechanism. The apparatus for image guidance includes:

a controlling module configured to control the imaging mechanism to rotate around the patient positioning mechanism;

a first acquiring module configured to acquire a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and an image guidance module configured to perform, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

In some possible embodiments, the capturing angles are a plurality of continuous capturing angles with the same angle interval, and the controlling module is further configured to:

control the imaging mechanism to rotate around the patient positioning mechanism at a constant speed, so that the imaging mechanism is continuously rotated to pass the capturing angles with the same time interval.

In some possible embodiments, the apparatus further includes:

a second acquiring module configured to acquire a two-dimensional projected image of a three-dimensional reconstructed image of the patient at each of the capturing angles, the three-dimensional reconstructed image being based on computed tomography;

correspondingly, the image guidance module includes:

a first registering unit configured to acquire a first registration result by performing 2D-2D registration between the first image and the two-dimensional projected image at the first capturing angle;

a second registering unit configured to acquire a second registration result by performing 2D-2D registration between the second image and the two-dimensional projected image at the second capturing angle; and a first correcting unit configured to correct a relative position deviation between the current position state of the patient and an initial position state of the patient based on the first registration result and the second registration result.

In some possible embodiments, the apparatus further includes:

a third acquiring module configured to acquire a three-dimensional magnetic resonance image of the patient, wherein a region range of at least one object of interest is marked in the three-dimensional magnetic resonance image;

a fourth acquiring module configured to acquire a three-dimensional reference image of the patient, wherein the three-dimensional reference image is a three-dimensional reconstructed image based on computed tomography; and a registering module configured to mark the region range of each object of interest in the three-dimensional reference image by performing 3D-3D registration between the three-dimensional magnetic resonance image and the three-dimensional reference image;

correspondingly, the image guidance module is further configured to:

perform image guidance using the three-dimensional reference image as an indicator of an initial position state of the patient and using the combination of the first image and the second image as the indicator of the current position state of the patient.

In some possible embodiments, the image guidance module includes:

a third registering unit configured to acquire a third registration result by performing 2D-3D registration between the three-dimensional reference image and the combination of the first image and the second image; and a second correcting unit configured to correct the relative position deviation between the current position state of the patient and the initial position state of the patient based on the third registration result.

In some possible embodiments, the apparatus further includes:

an error correcting module configured to perform error correction on the current position state of the patient indicated by the combination of the first image and the second image by using at least one dual two-dimensional image combination after acquiring at least one third image corresponding to the first image;

the dual two-dimensional image combination is a combination between the first image and one of the third images, the third image is a medical image of the patient captured by the imaging mechanism at a third capturing angle, and the third capturing angle is a capturing angle among the capturing angles which is at an angle smaller than a second preset angle with the second capturing angle.

In some possible embodiments, the error correcting module includes:

a calculating unit configured to calculate a state parameter indicating the current position state of the patient based on each dual two-dimensional image combination, respectively; and an error correcting unit configured to perform error correction on a state parameter calculated based on the combination of the first image and the second image by using the state parameter respectively corresponding to each dual two-dimensional image combination.

According to a third aspect of the present disclosure, a medical device is provided. The medical device includes a processor and a memory, the memory stores program instructions therein, and the processor is configured to invoke the program instructions in the memory to perform any foregoing method for image guidance.

According to a fourth aspect of the present disclosure, a computer-readable storage medium is provided. The computer-readable storage medium stores a computer program therein, the computer program includes program instructions, and the program instructions, when executed by a processor, enable the processor to perform any foregoing method for image guidance.

DETAILED DESCRIPTION

For clearer descriptions of the principles and advantages of the present disclosure, embodiments of the present disclosure are further described in detail hereinafter in conjunction with the accompanying drawings. Apparently, the described embodiments are merely a part of embodiments of the present disclosure rather than all embodiments. Unless otherwise defined, technical terms or scientific terms used in the present disclosure shall have general meanings understandable by those of ordinary skill in the art. Terms "first", "second" and similar words used in the present disclosure do not indicate any sequence, quantity or importance, but are only used for distinguishing different components.

In related art, when image guidance is performed by using an imaging apparatus, it is required to perform imaging on the target region of the patient at two different angles respectively to acquire a spatial moving and changing situation of the target region of the patient. If an angle between two imaging sections is too small, the acquired result has a large error. Therefore, the angle of a certain size, e.g., 90 degrees, between two imaging sections is kept to reduce the error. Since the imaging apparatus is required to rotate 90 degrees after each detection of the current position state, a time interval between two image acquisitions is very long, and the deviation generated in this period may not be corrected in time. With respect to these issues, the present disclosure provides the following embodiments.

Figure 1:
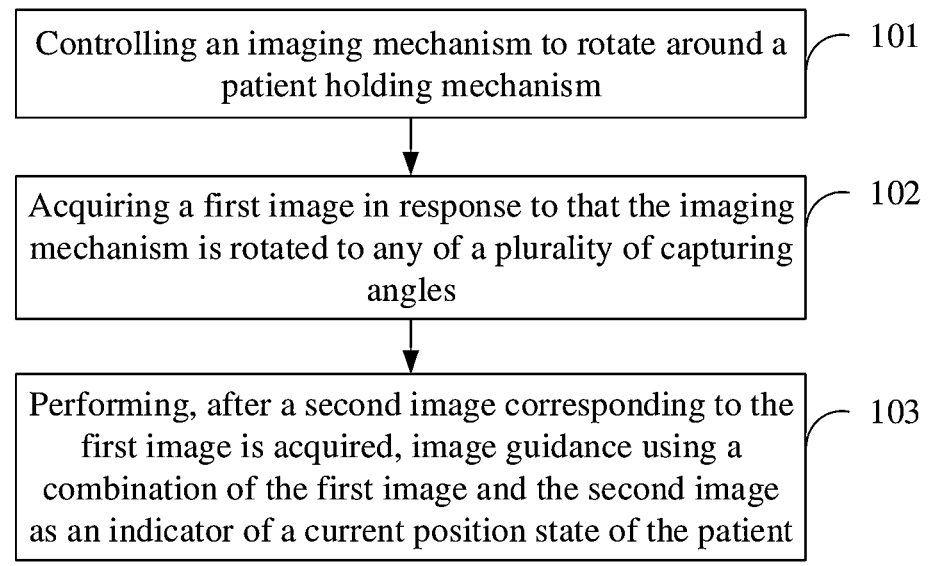
FIG. 1 is a flowchart of a method for image guidance according to an embodiment of the present disclosure.

FIG. 1 is a flowchart of a method for image guidance according to an embodiment of the present disclosure. The method for image guidance is applied to a medical device which includes a patient positioning mechanism and an imaging mechanism. The imaging mechanism is configured to be capable of capturing medical images of a patient on the patient positioning mechanism at a plurality of capturing angles by rotating around the patient positioning mechanism. In an example, the method for image guidance may be installed on a medical device (e.g., a medical device, an imaging device and an operating table) in the form of software to realize an image guidance process in a medical activity. In an example, an execution subject of the method may be, for example, a controller of the medical device, a processor of the medical device, a control apparatus connected to the medical device, or a server connected to the medical device, or the like. Referring to FIG. 1, the method for image guidance may include the following steps.

In 101, the imaging mechanism is controlled to rotate around the patient positioning mechanism.

In 102, a first image is acquired in response to that the imaging mechanism is rotated to any of a plurality of capturing angles.

The first image is a medical image of the patient captured by the imaging mechanism at a first capturing angle, and the first capturing angle is a capturing angle to which the imaging mechanism is currently rotated.

In 103, image guidance is performed using a combination of the first image and a second image as an indicator of a current position state of the patient after the second image corresponding to the first image is acquired.

The second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

It is to be noted that the method according to an embodiment of the present disclosure may be applied to any medical activity including image guidance, such as image-guided radio therapy (IGRT), intracerebral tumor resection or other surgeries related to image guidance. It is to be understood that the patients refer to implementation subjects of these medical activities, for example, patients requiring radiotherapy or surgery, and are not limited to people having diseases.

It is to be understood that the capturing angles may be, for example, capturing angles that are predetermined and required for medical image photographing according to usage needs (the capturing angle may be expressed as an angle value representing an orientation in plane polar coordinates, and an origin of the plane polar coordinates is a point surrounded by the imaging mechanism during rotation). For example, the capturing angles may be a plurality of capturing angles with an interval of 5 degrees, 10 degrees, 15 degrees, 20 degrees or 30 degrees in a range of 0 to 180 degrees within the same plane (for example, an exact right side of the patient may be selected as 0 degrees). The first preset angle is a predetermined angle value that avoids using two medical images at excessively close capturing angles for indicating the current position state of the patient, and may be selected in a range of, for example, 45 to 135 degrees.

Figure 2:
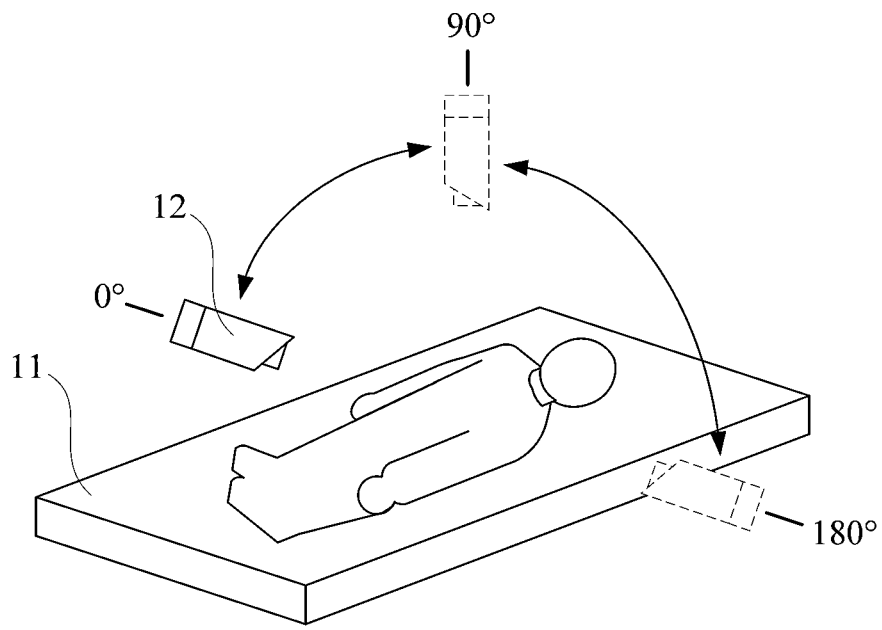
FIG. 2 is a schematic diagram of an application scenario of a method for image guidance according to an embodiment of the present disclosure.

FIG. 2 is a schematic diagram of an application scenario of a method for image guidance according to an embodiment of the present disclosure. Referring to FIG. 2, in this application scenario, the medical device includes a patient positioning mechanism 11 and an imaging mechanism 12. The patient positioning mechanism 11 includes a bed on which a patient may lie flatly, and the imaging mechanism 12 includes an X-ray detector for medical image photographing. It is to be understood that, based on the structure shown in FIG. 2, for example, to acquire medical images of X-ray transmitted images, the imaging mechanism 12 may further include an X-ray emitter that is always opposite to the X-ray detector, and may further include mechanical structures such as brackets, fasteners and/or guide rails for fixing the X-ray detector and the X-ray emitter; further, the mechanical structures may be a part of the patient positioning mechanism 11. As shown in FIG. 2, the imaging mechanism 12 may be rotated in a range of 180 degrees at a left side, front side and right side of the patient within a vertical plane, a capturing angle at the exact right side of the patient is 0 degrees, a capturing angle at the exact front side of the patient is 90 degrees, and a capturing angle at the exact left side of the patient is 180 degrees. Based on this, the ranges of the capturing angles may be determined according to usage needs and device limitations. In other possible embodiments, the imaging mechanism 12 may be rotated in a range of 360 degrees at the left side, front side, right side and back side of the patient, and the plane where a rotating trajectory of the imaging mechanism 12 is located may also be other planes such as a horizontal plane or inclined plane in addition to the vertical plane, which is not limited herein. Based on this, the application scenario and the medical device as shown in FIG. 2 are merely an example, and may be adaptively changed according to different usage needs. For example, the patient positioning mechanism 11 may also be a support used for fixing a patient in an upright posture, or the imaging mechanism 12 may be replaced with other types of imaging apparatuses of medical images, or the like, which is not enumerated herein.

Referring to the application scenario shown in FIG. 2, in an example, the capturing angles include 0 degrees, 30 degrees, 60 degrees, 90 degrees, 120 degrees, 150 degrees and 180 degrees from the exact right side to the exact left side of the patient, and the first preset angle is 90 degrees. A process of controlling the imaging mechanism 12 to rotate from 0 degrees to 180 degrees and then from 180 degrees to 0 degrees and to repeat such path at a constant speed may be included in the above 101. In this process, a medical image may be captured respectively by controlling the imaging mechanism 12 to rotate to each of the above capturing angles as described in the above 102. Since combinations of capturing angles satisfying the angle of 90 degrees include "0 degrees and 90 degrees", "30 degrees and 120 degrees", "60 degrees and 150 degrees" and "90 degrees and 180 degrees", no second image corresponding to the first image captured each time is acquired before the imaging mechanism 12 is rotated to 90 degrees for the first time; whereas, a second image corresponding to the first image captured each time is already acquired (a medical image previously acquired at a capturing angle may be covered by a medical image newly acquired at the capturing angle) from the imaging mechanism 12 is rotated to 90 degrees for the first time. Therefore, in response to that the imaging mechanism 12 is rotated to 90 degrees, 120 degrees, 150 degrees, 180 degrees and each subsequent capturing angle for the first time, image guidance may be performed using a combination of the first image and the corresponding second image as the indicator of the current position state of the patient as described in the above 103 after the first image is captured.

That is, in response to that the imaging mechanism 12 is rotated to 0 degrees, 30 degrees and 60 degrees for the first time, the medical image photographing process may be considered as a preparation process before normal start of the image guidance process, and an image guidance step may be performed after each photographing from the imaging mechanism 12 is rotated to 90 degrees for the first time (for example, registration is performed on the combination of the first image and the second image and the image indicating the initial position state of the patient, and the relative position deviation between the current position state of the patient and the initial position state of the patient is corrected based on a position offset acquired through registration). In this way, the detection of the current position state of the patient may be performed every time the imaging mechanism 12 is rotated 30 degrees, which is far more than a frequency of the detection performed every time the imaging mechanism 12 is rotated 90 degrees of the first preset angle.

It may be seen that, in the embodiments of the present disclosure, medical images at some capturing angles may be firstly acquired for use with the rotation of the imaging mechanism, and image guidance may be performed every time the imaging mechanism is rotated to a capturing angle, from the position being at the first preset angle with the initial position. In this way, the angle interval between two adjacent image guidance sections is the interval between two adjacent capturing angles. Compared to the prior art, the time interval between two adjacent detections of the current position state of the patient may be reduced, thereby improving the image guidance effect.

It is to be noted that a sequence in which the above 101, 102 and 103 are performed is not limited in the present disclosure, and may be arbitrarily disposed in a possible range.

Figure 3:
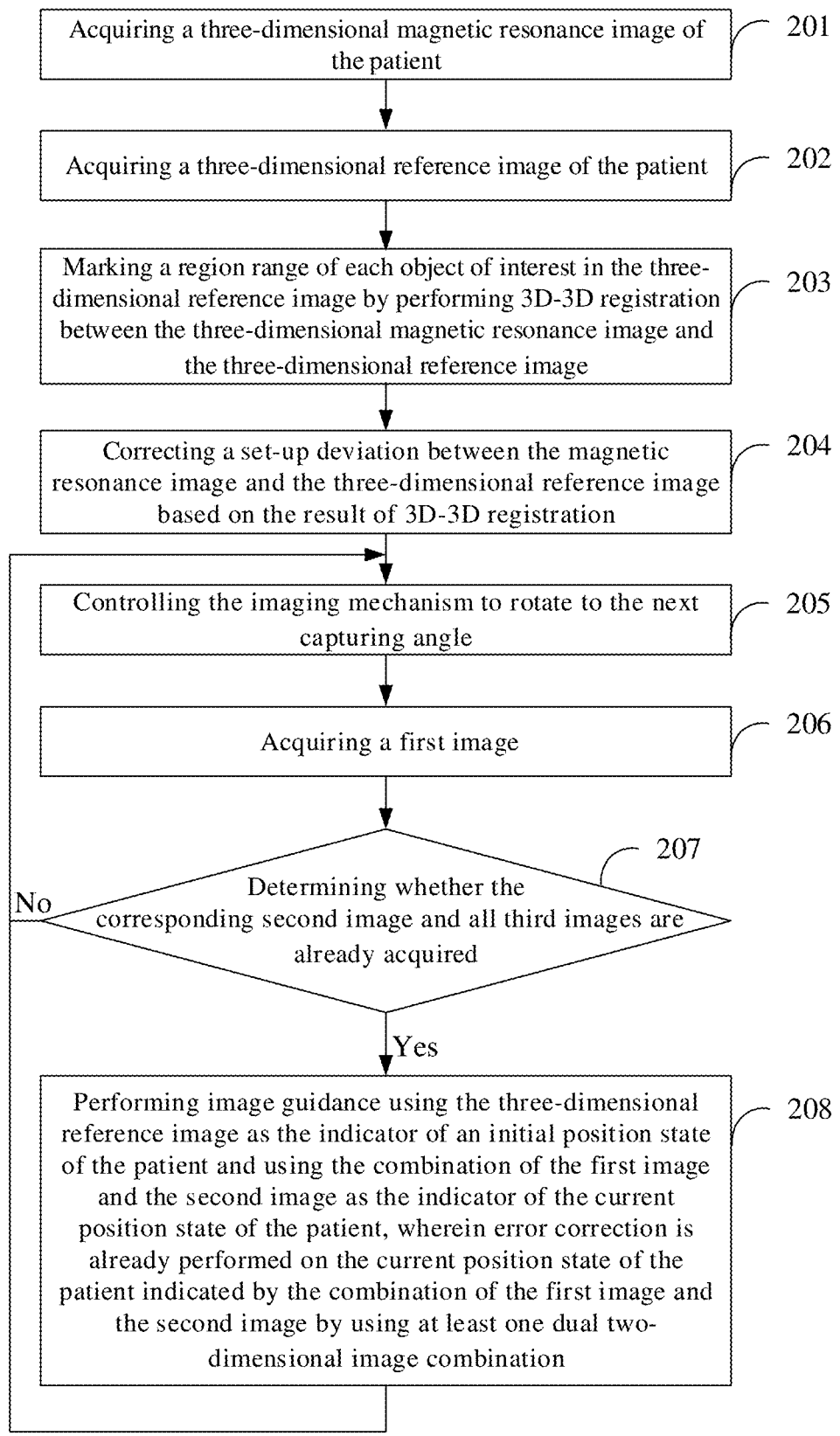
FIG. 3 is a flowchart of a method for image guidance according to another embodiment of the present disclosure.

FIG. 3 is a flowchart of a method for image guidance according to another embodiment of the present disclosure. In this embodiment, a controller in the medical device performs a method for image guidance to realize image-guided radiotherapy for a lung tumor. Referring to FIG. 3, the method for image guidance may include the following steps.

201 to 204 illustrate a process of detecting an initial position state of a patient. The initial position state of the patient refers to a position state of the patient before or at the beginning of a therapeutic activity, which corresponds to the current position state of the patient during the therapeutic activity (for example, two position states may be indicated by moving coordinates of a movable bed relative to a bottom supporting structure).

In 201, a three-dimensional magnetic resonance image of the patient is acquired.

A region range of at least one object of interest is marked in the three-dimensional magnetic resonance image.

The three-dimensional magnetic resonance (MR) image may be a three-dimensional image acquired by performing imaging on the patient mainly using an MRI technology, may be acquired by the above medical device from an imaging device through a communication connection, or may be acquired by the medical device performing imaging itself.

A user manually selects the region range of the object of interest, such as a region range of a lesion in radiotherapy, a position of a particular anatomical point, or a region range of a tumor and its surrounding vascular tissues in intracerebral tumor resection, in the magnetic resonance image. In an example, after receiving the three-dimensional magnetic resonance image, the above medical device displays the three-dimensional magnetic resonance image and provides a region selection tool, so that the user selects a region range of each object of interest through operations on the medical device. In another example, the above medical device receives the magnetic resonance image in which the region range of each object of interest is marked from the imaging device. Distribution features of soft tissues may be indicated clearly based on the magnetic resonance image, and the above region range of the object of interest marked in the magnetic resonance image has a higher precision than that in other types of images.

In an example, before treatment is started, medical personnel perform three-dimensional imaging on a chest of a patient (a patient with lung cancer) by operating an MRI device to acquire a three-dimensional magnetic resonance image of the chest of the patient, and then transmit the magnetic resonance image to a computer through a connection between devices. Next, the medical personnel draw each lesion zone in the magnetic resonance image as the region range of at least one object of interest marked in the above three-dimensional magnetic resonance image by operating the computer. In 201, the controller of the medical device receives the magnetic resonance image in which each lesion zone is marked from the computer device to acquire the three-dimensional magnetic resonance image.

In 202, a three-dimensional reference image of the patient is acquired.

The three-dimensional reference image is a three-dimensional reconstructed image based on computed tomography. The three-dimensional reference image is a three-dimensional image acquired through three-dimensional reconstruction after imaging is performed on the patient using a computed tomography (CT) imaging technology, may be received by the above medical device from the imaging device through the communication connection and acquired after processing, or may be received by the above medical device from an image processing device through a communication connection, or may be received by the medical device performing imaging itself and acquired after processing. The CT technology may be a cone beam CT (CBCT) technology, a singleslice helieal CT (SSCT) technology, a multislice helieal CT (MSCT) technology, or the like. The three-dimensional reference image may be compared with the combination of the first image and the second image acquired in real time in the subsequent image guidance process to provide information required for the medical activity, such as a deviation between the focus of a treatment beam and a target region position during radiotherapy, or whether a to-be-resected part moves during surgery.

In an example, before radiotherapy is started, medical personnel set up a patient before treatment, for example, change a posture and a position of the patient under the guidance of a laser line emitted from the medical device to enable the laser line to aim at the corresponding region of the patient. After set-up is completed, the medical personnel perform CBCT imaging on a chest of the patient by operating a CBCT system in the medical device. In 202, after imaging is completed, a control system of the medical device receives the acquired CBCT image data and perform three-dimensional reconstruction to acquire three-dimensional volume data of the chest of the patient as the above three-dimensional reference image. It is to be understood that since the three-dimensional reconstruction of the CBCT image may have cone-beam artifacts, the medical device may output a prompt to the user to guide the user to remove a part with image artifacts in the three-dimensional reference image (e.g., start and end of the CBCT image) in a step of selecting a region of interest (ROI) during the three-dimensional reconstruction, thereby facilitating increasing an accuracy of the CBCT image.

In 203, the region range of each object of interest is marked in the three-dimensional reference image by performing 3D-3D registration between the three-dimensional magnetic resonance image and the three-dimensional reference image.

The image registration refers to searching for one (or a series of) spatial transformation on one image to realize spatial consistence with corresponding points on the other image. That is, the above 3D-3D registration refers to searching for one or a series of spatial transformations to enable the magnetic resonance image to overlap with the three-dimensional reference image through such spatial transformation. It is to be noted that the 3D-3D registration may be performed only in a spatial region interested in the medical activity to save algorithm expenses; similarly, the magnetic resonance image and the three-dimensional reference image may also be acquired only in the spatial region interested in the medical activity to shorten imaging time and reduce an exposure dose. It is also to be noted that a result of image registration may be expressed as relative position coordinates of the same positioning point (or a point with the same name that may include, for example, an anatomical point or an image feature point) between images, or a transformation matrix between images, or a corresponding relationship table between different image regions with the same name in the image, which is not limited herein. Based on the result of the 3D-3D registration, the region range of at least one object of interest in the magnetic resonance image may be marked in the three-dimensional reference image. It may be understood that, as long as a registration precision satisfies application requirements, the region range of each object of interest may be marked in the three-dimensional reference image based on the registration result even if the object of interest indicated in the three-dimensional reference image is unclear or no object of interest is indicated.

In an example, the medical device acquires the magnetic resonance image and the three-dimensional reference image, and then performs 3D-3D image registration on the magnetic resonance image and the three-dimensional reference image. In an example, the above 3D-3D image registration includes searching for an optimal transformation relationship between the magnetic resonance image and the three-dimensional reference image in an iteration fashion, and taking the registration precision as a sign that instructs whether to continue the iteration. In response to that the registration precision reaches a designated level, the iteration is stopped, and the transformation relationship acquired through output is the registration result. Based on the transformation relationship of the registration result, the region range of each object of interest in the magnetic resonance image may be transformed into the region range of each object of interest in the three-dimensional reference image, so as to mark the region range of each object of interest in the three-dimensional reference image.

In an example, the maximum number of times of iteration is set in the above iteration process. In response to that the number of times of iteration reaches the maximum but the registration precision is still lower than the designated level, the iteration is stopped and a return is made to perform step 202 to reacquire the three-dimensional reference image. In this example, the above application condition, that is, "the registration precision reaches the designated level", may be set according to actual application requirements. It is to be understood that, in response to that the number of times of iteration reaches the maximum but the registration precision is still lower than the designated level, it may be considered that a difference between the three-dimensional reference image and the magnetic resonance image is excessively large at this time and it is difficult to find a reasonable image transformation relationship. Therefore, in this case, the three-dimensional reference image is reacquired and an intermediate process is repeated to increase an accuracy of the region range of each object of interest in the three-dimensional reference image based on ensuring the registration precision.

In 204, a set-up deviation between the magnetic resonance image and the three-dimensional reference image is corrected based on the result of 3D-3D registration.

In an example, in response to that the registration precision satisfies the application condition, the medical device may output the registration result to prompt the medical personnel to move the bed, so as to correct the set-up deviation between the three-dimensional reference image and the magnetic resonance image (that is, the deviation of the position state of the patient generated between capturing the three-dimensional reference image of the patient and capturing the magnetic resonance image of the patient). In a general case, it may be considered that the magnetic resonance image is standardized, so that the magnetic resonance image may represent a standard set-up position. Therefore, in response to that the registration precision of the three-dimensional reference image and the magnetic resonance image satisfies the application condition, it may be considered that the registration result represents the deviation between the current set-up position and the standard set-up position, so that the standard set-up position may be reached by moving the bed based on the registration result. The above process may facilitate reducing the set-up deviation.

The detection (a detection result is in the form of the three-dimensional reference image) and fixing of the initial position state of the patient are completed through the above process. Next, steps 205 to 208 illustrate a process of performing image guidance by detecting the current position state of the patient using the three-dimensional reference image as an indicator of an initial position state of the patient.

In 205, the imaging mechanism is controlled to rotate to the next capturing angle.

In an example, the controller of the medical device sends a rotation control instruction to the imaging mechanism through a connection with the imaging mechanism, so that the imaging mechanism is rotated based on the received rotation control instruction. After step 204, the controller may control the imaging mechanism to rotate to a start point among the capturing angles, for example, a capturing angle of 0 degrees in the above range of 0 degrees to 180 degrees.

In 206, a first image is acquired.

In an example, the controller controls the imaging mechanism to capture a medical image on lungs of the patient on the patient positioning mechanism at the current capturing angle through the connection with the imaging mechanism, and takes the medical image captured through the connection with the imaging mechanism as the current first image. Processing such as denoising, compression, filtering and feature extraction may be performed on the medical image. Then, the controller may store the acquired first image corresponding to the capturing angle in a memory.

In 207, whether a second image corresponding to the first image and all third images corresponding to the first image are acquired is determined.

The third image is a medical image of the patient captured by the imaging mechanism at a third capturing angle, and the third capturing angle is a capturing angle among the capturing angles which is at an angle smaller than a second preset angle with the second capturing angle. In an example, the first preset angle is 90 degrees, and the second preset angle is 10 degrees; thus, in response to that the first capturing angle is 130 degrees, the second capturing angle is 40 degrees, and the third capturing angle includes 30 degrees and 50 degrees. In an example, the controller may inquire whether medical images corresponding to the second capturing angle and each third capturing angle are stored in the memory according to a preset rule, so as to implement the above determination process. In response to that the medical images corresponding to the second capturing angle and each third capturing angle are stored in the memory, it is determined that the second image corresponding to the first image and all third images corresponding to the first image are already acquired, and step 208 is performed. In response to that no medical image corresponding to the second capturing angle or any one or more of the third capturing angles is stored in the memory, it is determined that the second image corresponding to the first image and all third images corresponding to the first image are not acquired, and a return is made to perform step 205 to start the process of controlling the imaging mechanism to rotate to the next capturing angle.

In 208, image guidance is performed using the three-dimensional reference image as an indicator of an initial position state of the patient and using the combination of the first image and the second image as the indicator of the current position state of the patient, wherein error correction is already performed on the current position state of the patient indicated by the combination of the first image and the second image by using at least one dual two-dimensional image combination.

The dual two-dimensional image combination is a combination between the first image and one of the third images. In an example, step 208 includes the following process: acquiring a third registration result by performing 2D-3D registration between the three-dimensional reference image and the combination of the first image and the second image; and correcting a relative position deviation between the current position state of the patient and the initial position state of the patient based on the third registration result.

The relative position deviation may come from an overall movement of the patient in a time period between capturing the three-dimensional reference image and capturing two medical images, or may come from a movement of internal tissues of the patient relative to the patient, which is not limited herein. In the application scenario of the above radiotherapy, the above relative position deviation specifically refers to a deviation between the current target region position and a reference position thereof (that is, a target region position determined based on the three-dimensional reference image). Certainly, in other application scenarios other than radiotherapy, the above relative position deviation may have different meanings, and the purpose of outputting the result of the above 2D-3D registration may not be limited to correcting the above relative position deviation (for example, may also be tracking a movement of an object inside the patient, or acquiring an actual resection situation of a to-be-resected part).

Each of the above 2D-3D registration process may include as follows: generating a digitally reconstructed radiograph (DRR) by using a ray casting algorithm based on the three-dimensional reference image at the first capturing angle and the second capturing angle corresponding to the dual two-dimensional image combination, respectively, comparing the acquired two digitally reconstructed radiographs in pairs with the above dual two-dimensional image combination, and optimizing spatial transformation parameters based on the comparison result, so as to regenerate two digitally reconstructed radiographs in pairs based on the optimized parameters and repeat the above process (iteration); and outputting the optimized spatial transformation parameters as the result of the 2D-3D registration in response to that a termination condition is satisfied.

The above process of correcting the relative position deviation may include the followings. Firstly, 2D-3D registration is performed between each dual two-dimensional image combination and the three-dimensional reference image respectively based on the above process. Then, a three-dimensional offset of a geometric center of a tumor region in the same spatial coordinate system (that is, a spatial offset vector of the geometric center of the tumor region relative to the initial position state of the patient) may be calculated based on each of the acquired 2D-3D registration results respectively. Finally, all of the acquired three-dimensional offsets may be averaged, and an irradiation position (field position) of a radioactive ray for treatment may be matched with the current position state of the patient based on the averaged three-dimensional offset (for example, the controller may control at least one of the moving positions of an apparatus for transmitting a radioactive ray for treatment and an apparatus for fixing a patient to implement the above process; in addition, the controller may also instruct an operator to move the bed or multi-leaf grating blades by outputting the registration result in real time so as to correct the position of the patient or the field position).

The tumor position may be tracked and the real-time image guidance may be realized by continuously repeating the processes of the above steps 205 to 208 with the rotation of the imaging mechanism. Certainly, a predetermined threshold may be set to compare with the above relative position deviation; in response to that the relative position deviation is greater than or equal to the predetermined threshold, no operation may be performed and the treatment may be continued. It is to be understood that the predetermined threshold may be determined according to actual application scenarios and application requirements.

It may be understood that, compared to the result of 2D-3D registration that is between the three-dimensional reference image and the combination of the first image and the second image and directly used to correct the relative position deviation, the registration result further in combination with a plurality of dual two-dimensional image combinations is more conducive to reducing the error.

Figure 4:
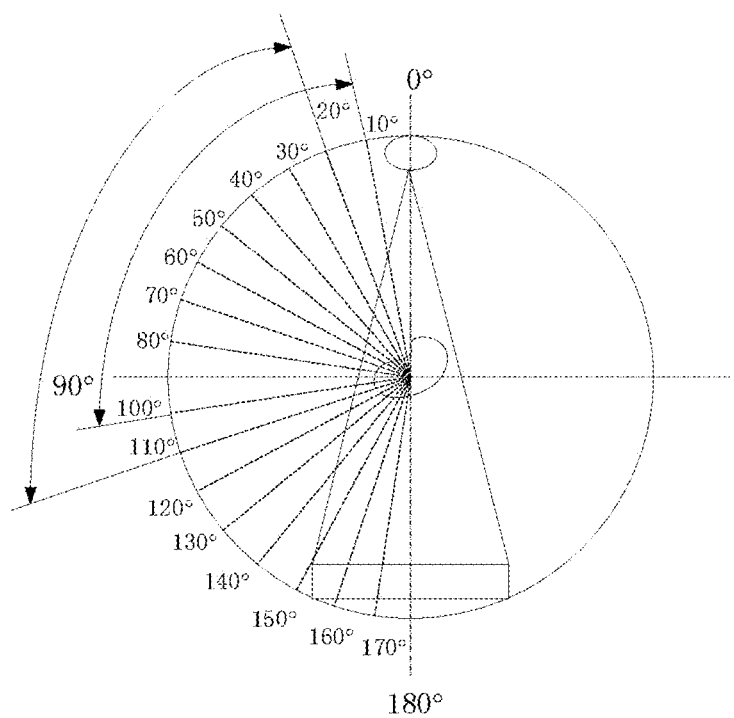
FIG. 4 is a schematic diagram of an implementation principle of a method for image guidance according to another embodiment of the present disclosure.

FIG. 4 is a schematic diagram of an implementation principle of a method for image guidance according to another embodiment of the present disclosure. Referring to FIG. 4, in an example, the capturing angles are 19 capturing angles having an angle interval being 10 degrees in a range of 0 degrees to 180 degrees, the first preset angle is 90 degrees, and the second preset angle is 10 degrees; the path in which the imaging mechanism is controlled to rotate described in the above step 205 is from 0 degrees to 180 degrees and then from 180 degrees to 0 degrees, and so on. Thus, the image guidance process performed by detecting the current position state of the patient in the above method for image guidance may include as follows: in response to that the imaging mechanism is rotated to each angle from 0 degrees to 100 degrees for the first time, since the corresponding medical images at three capturing angles (one second capturing angle and two third capturing angles) are not yet acquired, a process corresponding to the next capturing angle is performed after the first image is acquired (corresponding to FIG. 3, steps 205 and 206 are performed sequentially and In 207, a return made to perform step 205). From the imaging mechanism is rotated to 100 degrees for the first time, it may be determined in each subsequent step 207 that medical images corresponding to the current first image at three capturing angles are already acquired, so that step 208 may be performed every time the imaging mechanism is controlled to rotate to a first capturing angle; therefore, the detection of the current position state of the patient and the correction of the relative position deviation are performed with an interval of time required for the imaging mechanism to rotate 10 degrees in this period.

By repeating the processes of steps 205 to 208, treatment processes of all target points may be completed sequentially, so as to finally complete the entire image guidance process.

In still other embodiments, the initial position state of the patient may also be acquired through the following step performed before step 205: acquiring a two-dimensional projected image of a three-dimensional reconstructed image of the patient at each of the capturing angles, the three-dimensional reconstructed image being based on computed tomography. The fashion in which the three-dimensional reconstructed image based on computed tomography is acquired may be referred to the above fashion in which the three-dimensional reference image is acquired. In an example, the two-dimensional projected image at each of the capturing angles may be acquired by projecting the acquired three-dimensional reference image at the capturing angles respectively.

Correspondingly, performing image guidance using at least one dual two-dimensional image combination as the indicator of the current position state of the patient may include: acquiring a first registration result by performing 2D-2D registration between the first image and the two-dimensional projected image at the first capturing angle; acquiring a second registration result by performing 2D-2D registration between the second image and the two-dimensional projected image at the second capturing angle; and correcting a relative position deviation between the current position state of the patient and an initial position state of the patient based on the first registration result and the second registration result. In an example, a two-dimensional offset at 110 degrees may be acquired by performing 2D-2D registration on a medical image at 110 degrees as a first image and a two-dimensional projected image at 110 degrees; next, a two-dimensional offset at 10 degrees may be acquired by performing 2D-2D registration on a medical image at 10 degrees as a third image and a two-dimensional projected image at 10 degrees, a two-dimensional offset at 20 degrees may be acquired by performing 2D-2D registration on a medical image at 20 degrees as a second image and a two-dimensional projected image at 20 degrees, and a two-dimensional offset at 30 degrees may be acquired by performing 2D-2D registration on a medical image at 30 degrees as the third image and a two-dimensional projected image at 30 degrees; finally, a three-dimensional offset may be calculated by integrating the two-dimensional offsets at 10 degrees, 20 degrees, 30 degrees and 110 degrees, and the relative position deviation between the current position state of the patient and the initial position state of the patient may be corrected based on the three-dimensional offset in any of the above fashions.

It may be seen that, compared to the embodiment shown in FIG. 2, the region range of each object of interest may not be accurately positioned in this embodiment, thereby bringing certain difficulties and uncertainties to radiotherapy; further, since an initial set-up error cannot be corrected, an accuracy of the radiotherapy may be affected. Therefore, compared to this embodiment, accurate positioning of the region range of each object of interest may be provided by using a magnetic resonance image in the embodiment shown in FIG. 2, thereby helping correct the initial set-up error and enabling the radiotherapy to be more accurate and easier to perform.

In addition, the region range of the object of interest with a very high precision in the magnetic resonance image may be marked in the three-dimensional reference image by performing 3D-3D registration between the magnetic resonance image and the three-dimensional reference image in the embodiment shown in FIG. 2, so that the image guidance process in which the three-dimensional reference image is used to indicate the initial position state of the patient may take benefits from a high soft tissue contrast resolution of MRI, that is, the MRI is introduced into real-time image guidance, thereby performing the real-time image guidance better by means of advantages of the MRI technology.

In addition, it is to be noted that, based on any of the above examples, it is infeasible to directly replace the CBCT image with the magnetic resonance image as the three-dimensional reference image for the following main reasons. The above ray casting algorithm may simulate an attenuation and exposure process when an X-ray penetrates through different tissues and organs of a human body according to three-dimensional volume data acquired based on CBCT. The acquired CT value is expressed by a ratio of attenuation of the X-ray on tissues to attenuation of the X-ray on water.

$$\mu = (CT/1000 + 1) \cdot \mu_{water} \cdot F$$

In the above formula, F refers to a transformation factor, $\mu$ refers to an attenuation coefficient of the X-ray in tissues, and $\mu_{water}$ refers to an attenuation coefficient of the X-ray in water. Based on this, a cumulative attenuation parameter of each ray passing through the three-dimensional volume data may be calculated based on the three-dimensional volume data composed of different CT values passed by the X-ray.

$$I = I_0 \cdot e^{-\Sigma \mu_i l_i}$$

In the above formula, $I_0$ refers to an initial strength of the X-ray, $\mu_i$ refers to a linear attenuation coefficient of tissues i, $l_i$ refers to a length of the X-ray passing through the tissues i, and I refers to a strength of the X-ray passing through the three-dimensional volume data. Based on the above relationship, the three-dimensionally reconstructed CBCT image may be transformed into a two-dimensional digitally-reconstructed radiograph by transforming the above I into a gray value of the image. However, the magnetic resonance image reflects a hydrogen content of different tissues of the human body, and there is no relationship, similar to that of the above CT value and the attenuation coefficient of the tissues, between an MRI value of the image and the attenuation coefficient of the tissues. Even if three-dimensional volume data composed of MRI values passed by the ray is simulated and the cumulative attenuation parameter of each ray is calculated according to the above method for calculating a cumulative attenuation parameter, the acquired value may not correctly reflect density attenuation information of different tissues, and registration cannot be accurately performed between the magnetic resonance image and the X-ray transmitted image acquired in real time either.

Based on the above reasons, the MRI generally may not be applied to real-time image guidance, and the high soft tissue contrast resolution of MRI is not beneficial to the image guidance effect either. However, 3D-3D registration between the magnetic resonance image and the three-dimensional reference image is used in the embodiment of the present disclosure, so that advantages of MRI can be indirectly applied to the real-time image guidance through the three-dimensional reference image; thus, the real-time image guidance is not required to repeat a large number of time-consuming imaging processes for MRI, and may take benefits from the advantages of MRI, thereby facilitating realizing the real-time image guidance with a better effect.

It is to be noted that, in other possible embodiments, the number of third images corresponding to each first image may also be, for example, three, four, five or six according to different second preset angles. When error correction is performed by using at least one third image, the current position state of the patient may be indicated based on two medical images of the first image and the second image, and the error may also be reduced by averaging a plurality of detection results.

Figure 5:
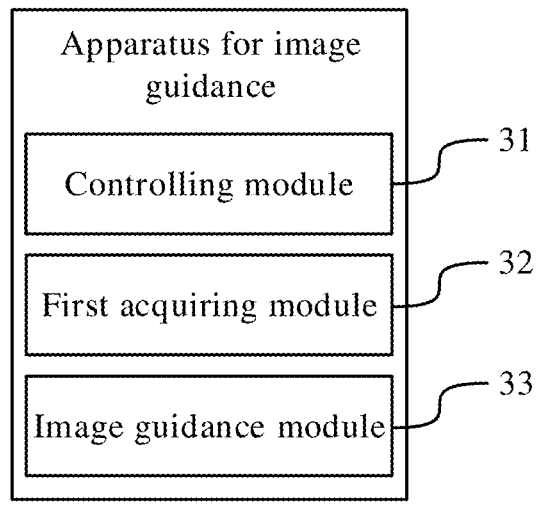
FIG. 5 is a structural block diagram of an apparatus for image guidance according to an embodiment of the present disclosure.

FIG. 5 is a structural block diagram of an apparatus for image guidance according to an embodiment of the present disclosure. The apparatus for image guidance is applied to a medical device which includes a patient positioning mechanism and an imaging mechanism. The imaging mechanism is configured to be capable of capturing medical images of a patient on the patient positioning mechanism at a plurality of capturing angles by rotating around the patient positioning mechanism. In an example, the method for image guidance may be installed on a medical device (e.g., a medical device, an imaging device and an operating table) in the form of software to realize an image guidance process in a medical activity. Referring to FIG. 5, the apparatus for image guidance includes:

a controlling module 31 configured to control the imaging mechanism to rotate around the patient positioning mechanism;

a first acquiring module 32 configured to acquire a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and an image guidance module 33 configured to perform, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

In some possible embodiments, the capturing angles are a plurality of continuous capturing angles with the same angle interval, and the controlling module 31 is further configured to:

control the imaging mechanism to rotate around the patient positioning mechanism at a constant speed, so that the imaging mechanism is continuously rotated to pass the capturing angles with the same time interval.

In some possible embodiments, the apparatus further includes:

a second acquiring module configured to acquire a two-dimensional projected image of a three-dimensional reconstructed image of the patient at each of the capturing angles, the three-dimensional reconstructed image being based on computed tomography;

correspondingly, the image guidance module 33 includes:

a first registering unit configured to acquire a first registration result by performing 2D-2D registration between the first image and the two-dimensional projected image at the first capturing angle;

a second registering unit configured to acquire a second registration result by performing 2D-2D registration between the second image and the two-dimensional projected image at the second capturing angle; and a first correcting unit configured to correct a relative position deviation between the current position state of the patient and an initial position state of the patient based on the first registration result and the second registration result.

In some possible embodiments, the apparatus further includes:

a third acquiring module configured to acquire a three-dimensional magnetic resonance image of the patient, wherein a region range of at least one object of interest is marked in the three-dimensional magnetic resonance image;

a fourth acquiring module configured to acquire a three-dimensional reference image of the patient, wherein the three-dimensional reference image is a three-dimensional reconstructed image based on computed tomography; and a registering module configured to mark the region range of each object of interest in the three-dimensional reference image by performing 3D-3D registration between the three-dimensional magnetic resonance image and the three-dimensional reference image;

correspondingly, the image guidance module 33 is further configured to:

perform image guidance using the three-dimensional reference image as an indicator of an initial position state of the patient and using the combination of the first image and the second image as the indicator of the current position state of the patient.

In some possible embodiments, the image guidance module 33 includes:

a third registering unit configured to acquire a third registration result by performing 2D-3D registration between the three-dimensional reference image and the combination of the first image and the second image; and a second correcting unit configured to correct the relative position deviation between the current position state of the patient and the initial position state of the patient based on the third registration result.

In some possible embodiments, the apparatus further includes:

an error correcting module configured to perform error correction on the current position state of the patient indicated by the combination of the first image and the second image by using at least one dual two-dimensional image combination after acquiring at least one third image corresponding to the first image;

the dual two-dimensional image combination is a combination between the first image and one of the third images, the third image is a medical image of the patient captured by the imaging mechanism at a third capturing angle, and the third capturing angle is a capturing angle among the capturing angles which is at an angle smaller than a second preset angle with the second capturing angle.

In some possible embodiments, the error correcting module includes:

a calculating unit configured to calculate a state parameter indicating the current position state of the patient based on each dual two-dimensional image combination, respectively; and an error correcting unit configured to perform error correction on a state parameter calculated based on the combination of the first image and the second image by using the state parameter respectively corresponding to each dual two-dimensional image combination.

It is to be understood that the apparatus for image guidance may implement any foregoing method for image guidance through the corresponding structures and configurations based on optional embodiments of the method for image guidance described above, and the details are not repeated herein.

In an example corresponding to FIG. 5, the apparatus for image guidance is embodied in the form of functional units/functional modules. The "unit/module" herein may be an application specific integrated circuit (ASIC), a processor executing one or more software or firmware programs and a memory, an integrated logic circuit, and/or another device that may provide the foregoing functions. For example, at least some functions of at least one of the units and modules may be implemented by a processor executing a program code stored in the memory.

Figure 6:
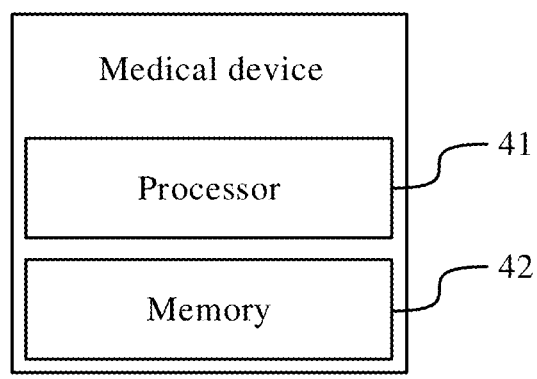
FIG. 6 is a structural block diagram of a medical device according to an embodiment of the present disclosure.

FIG. 6 is a structural block diagram of a medical device according to an embodiment of the present disclosure. Referring to FIG. 6, the medical device includes a processor 41 and a memory 42. The memory 42 stores program instructions therein. The processor 41 is configured to invoke the program instructions in the memory 42 to perform any foregoing method for image guidance.

The processor 41 may include a central processing unit (CPU, a single core or multi-core CPU), a graphics processing unit (GPU), a microprocessor, an application-specific integrated circuit (ASIC), a digital signal processor (DSP), a digital signal processing device (DSPD), a programmable logic device (PLD), a field-programmable gate array (FPGA), a controller, a microcontroller, or a plurality of integrated circuits configured to control the execution of a program.

The memory 42 may include a read-only memory (ROM) or another type of static storage device that may store static information and instructions, a random access memory (RAM) or another type of dynamic storage device that may store information and instructions, or may include an electrically erasable programmable read-only memory (EEPROM), a compact disc read-only memory (CD-ROM) or another optical disc storage, a disc storage (including a compact disc, a laser disc, a disc, a digital versatile disc, a blue-ray disc, or the like), a magnetic disk storage medium or another magnetic storage device, or any other medium that can be configured to carry or store an expected program code in the form of instructions or a data structure and can be accessed by a computer, but is not limited thereto. The memory may be disposed independently or may be integrated with a processor.

During specific implementation, in an embodiment, the processor 41 may include one or more CPUs. During specific implementation, in an embodiment, the above medical device may include a plurality of processors. Each of these processors may be a single-CPU processor or may be a multi-CPU processor. The processor herein may be one or more devices, circuits, and/or processing cores configured to process data (for example, computer program instructions).

The above medical device may include a general-purpose computer device or a special-purpose computer device. During specific implementation, the medical device may be any electronic device that requires medical image imaging registration, for example, a radiotherapy device, an image guidance medical device, an operating table, or the like. The computer device may be a desktop computer, a portable computer, a network server, a personal digital assistant (PDA), a mobile phone, a tablet computer, a wireless terminal device, a communication device, an embedded device or a device with a similar structure.

An embodiment of the present disclosure further provides a computer-readable storage medium, configured to store a computer program used for any foregoing method for image guidance. The computer program includes program instructions. The stored program may be executed to implement any foregoing method for image guidance according to the present disclosure.

A person skilled in the art should understand that embodiments of the present disclosure may be provided as a method, an apparatus (a device) or a computer program product. Therefore, the present disclosure may use a form of hardware only embodiments, software only embodiments, or embodiments with a combination of software and hardware. Moreover, the present disclosure may use a form of a computer program product that is implemented on one or more computer-usable storage media (including but not limited to a disk memory, a CD-ROM, an optical memory, and the like) that include a computer-usable program code. The computer program is stored/distributed in an appropriate medium, and is provided together with other hardware or used as a part of hardware, or may use another distribution form, for example, the internet or another wired or wireless telecommunication system.

The present disclosure is described with reference to the flowcharts and/or block diagrams of the method, the apparatus (device), and the computer program product in the embodiments of the present disclosure. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a special-purpose computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may also be stored in a computer-readable memory that can instruct the computer or any other programmable data processing device to work in a specific fashion, so that the instructions stored in the computer-readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, so that a series of operations and steps are performed on the computer or the other programmable device, thereby generating computer-implemented processing. Therefore, the instructions executed on the computer or the other programmable device provide steps for implementing a specific function in one or more processes in the flowcharts and/or in one or more blocks in the block diagrams.

The foregoing is merely embodiments of the present disclosure but is not used to limit the present disclosure. Any changes, equivalent replacements, improvements, and the like made within the spirit and principle of the present disclosure shall fall within the protection scope of the claims of the present disclosure.

What is claimed is:

1. A method for image guidance, applied to a medical device, wherein the medical device comprises a patient positioning mechanism and an imaging mechanism, the imaging mechanism is configured to be capable of capturing medical images of a patient on the patient positioning mechanism at a plurality of capturing angles by rotating around the patient positioning mechanism; and the method comprises:

controlling the imaging mechanism to rotate around the patient positioning mechanism;

acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and performing, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is one of the capturing angles, the second capturing angle is at a first preset angle with the first capturing angle, and an angle interval between any two adjacent capturing angles among the capturing angles is smaller than the first preset angle.

2. The method according to claim 1, wherein the capturing angles are a plurality of continuous capturing angles with the same angle interval, the first preset angle is an integer multiple of the angle interval between any two adjacent capturing angles among the capturing angles, and controlling the imaging mechanism to rotate around the patient positioning mechanism comprises:

controlling the imaging mechanism to rotate around the patient positioning mechanism at a constant speed, so that the imaging mechanism is continuously rotated to pass the capturing angles with the same time interval.

3. The method according to claim 1, further comprising:

acquiring a two-dimensional projected image of a three-dimensional reconstructed image of the patient at each of the capturing angles, the three-dimensional reconstructed image being based on computed tomography, wherein correspondingly, performing image guidance using the combination of the first image and the second image as the indicator of the current position state of the patient comprises:
acquiring a first registration result by performing 2D-2D registration between the first image and the two-dimensional projected image at the first capturing angle;
acquiring a second registration result by performing 2D-2D registration between the second image and the two-dimensional projected image at the second capturing angle; and
correcting a relative position deviation between the current position state of the patient and an initial position state of the patient based on the first registration result and the second registration result.

4. The method according to claim 1, further comprising:
acquiring a three-dimensional magnetic resonance image of the patient, wherein a region range of at least one object of interest is marked in the three-dimensional magnetic resonance image;
acquiring a three-dimensional reference image of the patient, wherein the three- dimensional reference image is a three-dimensional reconstructed image based on computed tomography; and
marking a region range of each object of interest in the three-dimensional reference image by performing 3D-3D registration between the three-dimensional magnetic resonance image and the three-dimensional reference image, wherein
correspondingly, performing image guidance using the combination of the first image and the second image as the indicator of the current position state of the patient comprises:
performing image guidance using the three-dimensional reference image as an indicator of an initial position state of the patient and using the combination of the first image and the second image as the indicator of the current position state of the patient.

5. The method according to claim 4, wherein performing image guidance using the three-dimensional reference image as the indicator of the initial position state of the patient and using the combination of the first image and the second image as the indicator of the current position state of the patient comprises:
acquiring a third registration result by performing 2D-3D registration between the three-dimensional reference image and the combination of the first image and the second image; and
correcting the relative position deviation between the current position state of the patient and the initial position state of the patient based on the third registration result.

6. The method according to claim 1, further comprising:
performing error correction on the current position state of the patient indicated by the combination of the first image and the second image by using at least one dual two-dimensional image combination after at least one third image corresponding to the first image is acquired, wherein
the dual two-dimensional image combination is a combination between the first image and one of the third images, the third image is a medical image of the patient captured by the imaging mechanism at a third capturing angle, and the third capturing angle is a capturing angle among the capturing angles which is at an angle smaller than a second preset angle with the second capturing angle.

7. The method according to claim 6, wherein performing error correction on the current position state of the patient indicated by the combination of the first image and the second image by using at least one dual two-dimensional image combination comprises:
calculating a state parameter indicating the current position state of the patient based on each dual two-dimensional image combination, respectively; and
performing error correction on a state parameter calculated based on the combination of the first image and the second image by using the state parameter respectively corresponding to each dual two-dimensional image combination.

8. A non-transitory computer-readable storage medium storing a computer program therein, wherein the computer program comprises program instructions, and the program instructions, when executed by a processor, enable the processor to perform a method for image guidance comprising:
controlling an imaging mechanism to rotate around a patient positioning mechanism, wherein the imaging mechanism is configured to be capable of capturing medical images of a patient on the patient positioning mechanism at a plurality of capturing angles by rotating around the patient positioning mechanism;
acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and
performing, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

9. A medical device, comprising a processor and a memory, wherein the memory stores program instructions therein, and the processor is configured to execute the program instructions in the memory to perform a method for image guidance comprising:
controlling an imaging mechanism to rotate around a patient positioning mechanism, wherein the imaging mechanism is configured to be capable of capturing medical images of a patient on the patient positioning mechanism at a plurality of capturing angles by rotating around the patient positioning mechanism;
acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and
performing, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

10. The medical device according to claim 9, wherein the capturing angles are a plurality of continuous capturing angles with the same angle interval, the first preset angle is an integer multiple of the angle interval between any two adjacent capturing angles among the capturing angles, and controlling the imaging mechanism to rotate around the patient positioning mechanism comprises:

controlling the imaging mechanism to rotate around the patient positioning mechanism at a constant speed, so that the imaging mechanism is continuously rotated to pass the capturing angles with the same time interval.

11. The medical device according to claim 9, wherein the method further comprises:

acquiring a two-dimensional projected image of a three-dimensional reconstructed image of the patient at each of the capturing angles, the three-dimensional reconstructed image being based on computed tomography, wherein correspondingly, performing image guidance using the combination of the first image and the second image as the indicator of the current position state of the patient comprises:

acquiring a first registration result by performing 2D-2D registration between the first image and the two-dimensional projected image at the first capturing angle;

acquiring a second registration result by performing 2D-2D registration between the second image and the two-dimensional projected image at the second capturing angle; and correcting a relative position deviation between the current position state of the patient and an initial position state of the patient based on the first registration result and the second registration result.

12. The medical device according to claim 9, wherein the method further comprises:

acquiring a three-dimensional magnetic resonance image of the patient, wherein a region range of at least one object of interest is marked in the three-dimensional magnetic resonance image;

acquiring a three-dimensional reference image of the patient, wherein the three-dimensional reference image is a three-dimensional reconstructed image based on computed tomography; and marking a region range of each object of interest in the three-dimensional reference image by performing 3D-3D registration between the three-dimensional magnetic resonance image and the three-dimensional reference image, wherein correspondingly, performing image guidance using the combination of the first image and the second image as the indicator of the current position state of the patient comprises:

performing image guidance using the three-dimensional reference image as an indicator of an initial position state of the patient and using the combination of the first image and the second image as the indicator of the current position state of the patient.

13. The medical device according to claim 12, wherein performing image guidance using the three-dimensional reference image as the indicator of the initial position state of the patient and using the combination of the first image and the second image as the indicator of the current position state of the patient comprises:

acquiring a third registration result by performing 2D-3D registration between the three-dimensional reference image and the combination of the first image and the second image; and correcting the relative position deviation between the current position state of the patient and the initial position state of the patient based on the third registration result.

14. The medical device according to claim 9, wherein the method further comprises:

performing error correction on the current position state of the patient indicated by the combination of the first image and the second image by using at least one dual two-dimensional image combination after at least one third image corresponding to the first image is acquired, wherein the dual two-dimensional image combination is a combination between the first image and one of the third images, the third image is a medical image of the patient captured by the imaging mechanism at a third capturing angle, and the third capturing angle is a capturing angle among the capturing angles which is at an angle smaller than a second preset angle with the second capturing angle.

15. The medical device according to claim 14, wherein performing error correction on the current position state of the patient indicated by the combination of the first image and the second image by using at least one dual two-dimensional image combination comprises:

calculating a state parameter indicating the current position state of the patient based on each dual two-dimensional image combination, respectively; and performing error correction on a state parameter calculated based on the combination of the first image and the second image by using the state parameter respectively corresponding to each dual two-dimensional image combination.

16. A medical device, comprising a patient positioning mechanism, an imaging mechanism, a processor and a memory, wherein the imaging mechanism is configured to be capable of capturing medical images of a patient on the patient positioning mechanism at a plurality of capturing angles by rotating around the patient positioning mechanism, the memory stores program instructions therein, and the processor is configured to execute the program instructions in the memory to perform a method for image guidance comprising:

controlling the imaging mechanism to rotate around the patient positioning mechanism;

acquiring a first image in response to that the imaging mechanism is rotated to any one of the capturing angles, the first image being a medical image of the patient captured by the imaging mechanism at a first capturing angle, and the first capturing angle being a capturing angle to which the imaging mechanism is currently rotated; and performing, after a second image corresponding to the first image is acquired, image guidance using a combination of the first image and the second image as an indicator of a current position state of the patient, wherein the second image is a medical image of the patient captured by the imaging mechanism at a second capturing angle, the second capturing angle is a capturing angle among the capturing angles which is at a first preset angle with the first capturing angle, and an angle interval between any two adjacent capturing angles among the capturing angles is smaller than the first preset angle.

17. The medical device according to claim 16, wherein the capturing angles are a plurality of continuous capturing angles with the same angle interval, the first preset angle is an integer multiple of the angle interval between any two adjacent capturing angles among the capturing angles, and controlling the imaging mechanism to rotate around the patient positioning mechanism comprises:
controlling the imaging mechanism to rotate around the patient positioning mechanism at a constant speed, so that the imaging mechanism is continuously rotated to pass the capturing angles with the same time interval.

18. The medical device according to claim 16, wherein the method further comprises:
acquiring a two-dimensional projected image of a three-dimensional reconstructed image of the patient at each of the capturing angles, the three-dimensional reconstructed image being based on computed tomography, wherein
correspondingly, performing image guidance using the combination of the first image and the second image as the indicator of the current position state of the patient comprises:
acquiring a first registration result by performing 2D-2D registration between the first image and the two-dimensional projected image at the first capturing angle;
acquiring a second registration result by performing 2D-2D registration between the second image and the two-dimensional projected image at the second capturing angle; and
correcting a relative position deviation between the current position state of the patient and an initial position state of the patient based on the first registration result and the second registration result.

19. The medical device according to claim 16, wherein the method further comprises:
acquiring a three-dimensional magnetic resonance image of the patient, wherein a region range of at least one object of interest is marked in the three-dimensional magnetic resonance image;
acquiring a three-dimensional reference image of the patient, wherein the three- dimensional reference image is a three-dimensional reconstructed image based on computed tomography; and
marking a region range of each object of interest in the three-dimensional reference image by performing 3D-3D registration between the three-dimensional magnetic resonance image and the three-dimensional reference image, wherein
correspondingly, performing image guidance using the combination of the first image and the second image as the indicator of the current position state of the patient comprises:
performing image guidance using the three-dimensional reference image as an indicator of an initial position state of the patient and using the combination of the first image and the second image as the indicator of the current position state of the patient.

20. The medical device according to claim 19, wherein performing image guidance using the three-dimensional reference image as the indicator of the initial position state of the patient and using the combination of the first image and the second image as the indicator of the current position state of the patient comprises:
acquiring a third registration result by performing 2D-3D registration between the three- dimensional reference image and the combination of the first image and the second image; and correcting the relative position deviation between the current position state of the patient and the initial position state of the patient based on the third registration result.

* * * * *